United States Patent [19]
Tamura

[11] Patent Number: 5,220,911
[45] Date of Patent: Jun. 22, 1993

[54] ARTICULATED PIPE WITH SHAPE MEMORY JOINT PIN

[75] Inventor: Hisaaki Tamura, Ootawara, Japan

[73] Assignee: Kabushiki Kaisha Toshiba, Kawasaki, Japan

[21] Appl. No.: 757,349

[22] Filed: Sep. 10, 1991

[30] Foreign Application Priority Data

Sep. 11, 1990 [JP] Japan .................. 2-241587

[51] Int. Cl.$^5$ ............................................. A61B 1/04
[52] U.S. Cl. ......................................... 128/4; 128/6;
604/281; 138/DIG. 7; 138/DIG. 8
[58] Field of Search ................ 128/4, 6; 604/281;
138/120, 159, DIG. 7, DIG. 8, DIG. 11

[56] References Cited

U.S. PATENT DOCUMENTS

| 4,712,133 | 12/1987 | Kikuchi .................. 128/4 |
| 4,807,596 | 2/1989 | Hochberger et al. .......... 128/4 |
| 4,869,585 | 9/1989 | Romanet . |
| 4,905,666 | 3/1990 | Fukuda .................. 128/4 |
| 4,977,902 | 12/1990 | Sekino et al. .......... 128/12 AA X |
| 5,078,684 | 1/1992 | Yasuda .............. 604/281 X |

Primary Examiner—V. Millin
Assistant Examiner—J. Doyle
Attorney, Agent, or Firm—Foley & Lardner

[57] ABSTRACT

An articulated pipe used for an endoscope includes articular chips made of brittle material such as a ceramic, with joint pins for joining the articular chips in series. The joint pins are made of shape-memory material. With these joint pins, the brittle articular chips are easily joined together without being damaged.

12 Claims, 11 Drawing Sheets

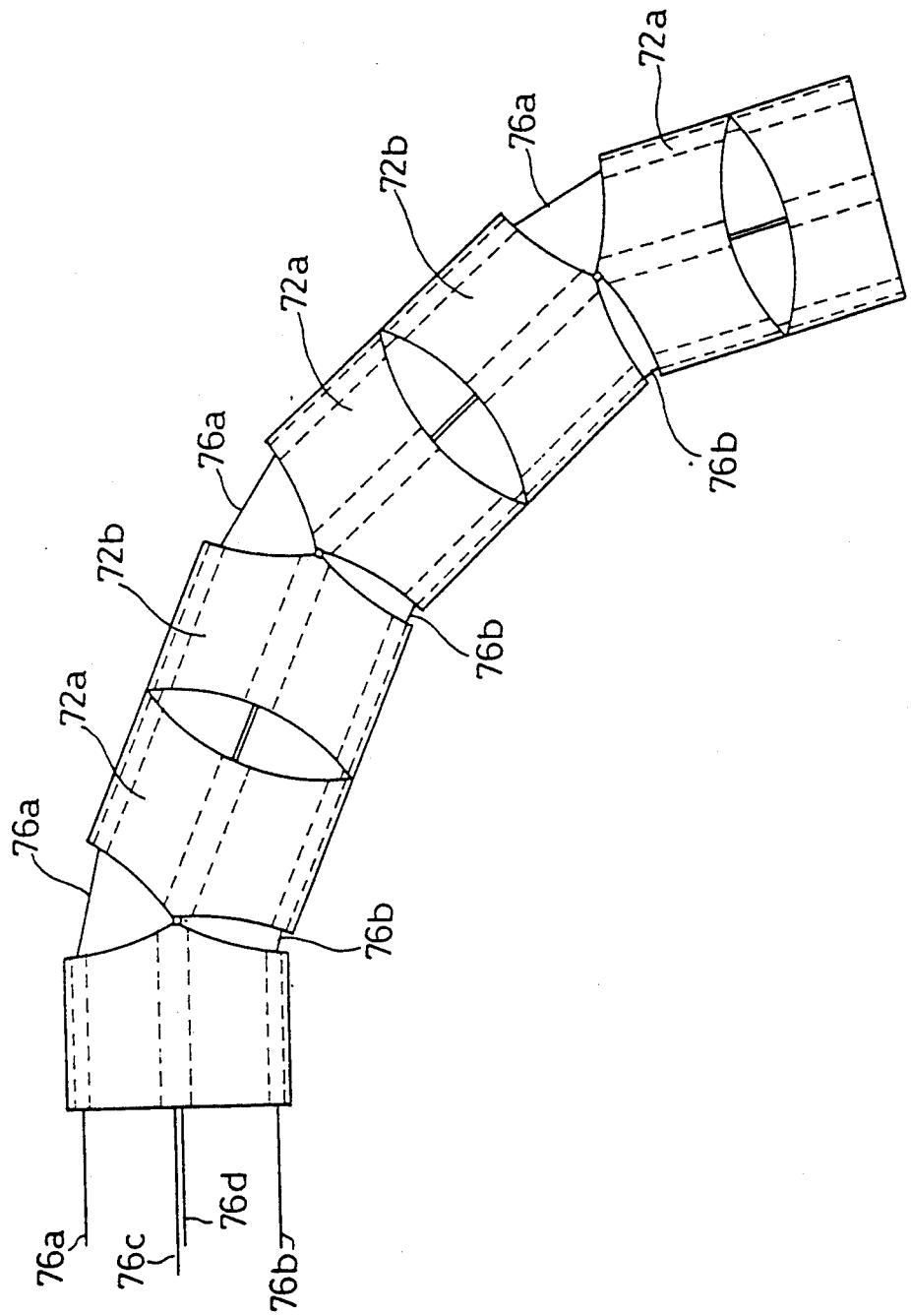

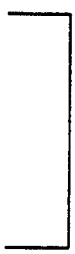
FIG.7(a)  FIG.7(b)         FIG.7(c)
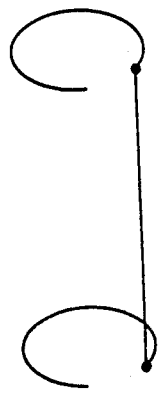
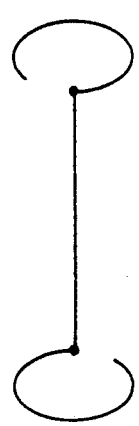
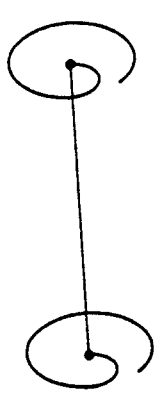
FIG.7(d)        FIG.7(e)        FIG.7(f)

ARTICULATED PIPE WITH SHAPE MEMORY JOINT PIN

BACKGROUND OF THE INVENTION

1. Field of the Invention

The present invention relates to a mechanism for inserting and guiding an flexible endoscopic tube provided with a sensor, such as a photographing element, to a target position in a human body cavity, and particularly to a mechanism for horizontally and vertically controlling a part of the flexible tube.

2. Description of the Prior Art

The flexible tube employed in an endoscope has a sensor at its head end, which is inserted into a body cavity, to observe, diagnose and treat the target area.

Since the human body cavity has complex curves, the flexible tube is bent along these curves of the body cavity by the operator's manipulation. To achieve this, at the head portion of the flexible tube, an articulated pipe is provided, composed of cylindrical articular chips joined in series with joint pins. This articulated pipe enables the flexible tube to be inserted along the human body cavity.

The articular chips are preferably made of metals, and joint pins for joining the articular chips, for example, rivets made of stainless steel. A metal has disadvantages in that it has a high friction factor and is easily abraded and corroded.

A desirable material for articular chips might be ceramics having a low friction factor. Toughness of the ceramics, however, is inferior to that of metals, so that, when the ceramic articular chips are joined together by hitting the joint pins with a hammer to deform for complete coupling of the articular chips, the ceramic articular chips may be easily damaged.

SUMMARY OF THE INVENTION

An object of the present invention is to solve this problem, that is, to provide a means for joining articular chips made of brittle material such as ceramics without breaking them when they are joined together with joint pins.

In order to accomplish to the object, the articulated pipe of the present invention is composed of articular chips made of ceramics or something similar for smooth insertion along the body cavity, whether curving vertically or horizontally. The articular chips have joint portions where they are joined in series with joint pins made of shape-memory material.

According to the present invention, the joint pins made of the shape-memory material that memorizes a required shape in preprocessing. The joint pins memorizing the required shape are processed into the shape that can be easily inserted into the joint portion of the articular chips. After inserting into the joint portion, the joint pins are heated to restore the memorized shape.

In this way, the articular chips are joined with one another with joint pins without applying shocks to the articular chips. The articular chips made of brittle material, therefore, will not be broken during the joining process.

According the present invention, as explained above, the articular chips made of brittle material are joined with one another with joint pins made of shape-memory material, thereby forming the articulated pipe without damaging the articular chips.

These and other objects, features and advantages of the present invention will be more apparent from the following description of a preferred embodiment in conjunction with the accompanying drawings.

BRIEF DESCRIPTION OF THE DRAWINGS

FIG. 6 is an explanatory view showing a bending operation of the articulated pipe;

FIGS. 7(a) to 7(f) and 8(a) to 8(c) are views showing shaped memorized in joint pins used for joining the articulated pipe according to the invention.

DETAILED DESCRIPTION OF THE EMBODIMENTS

Figure 1:
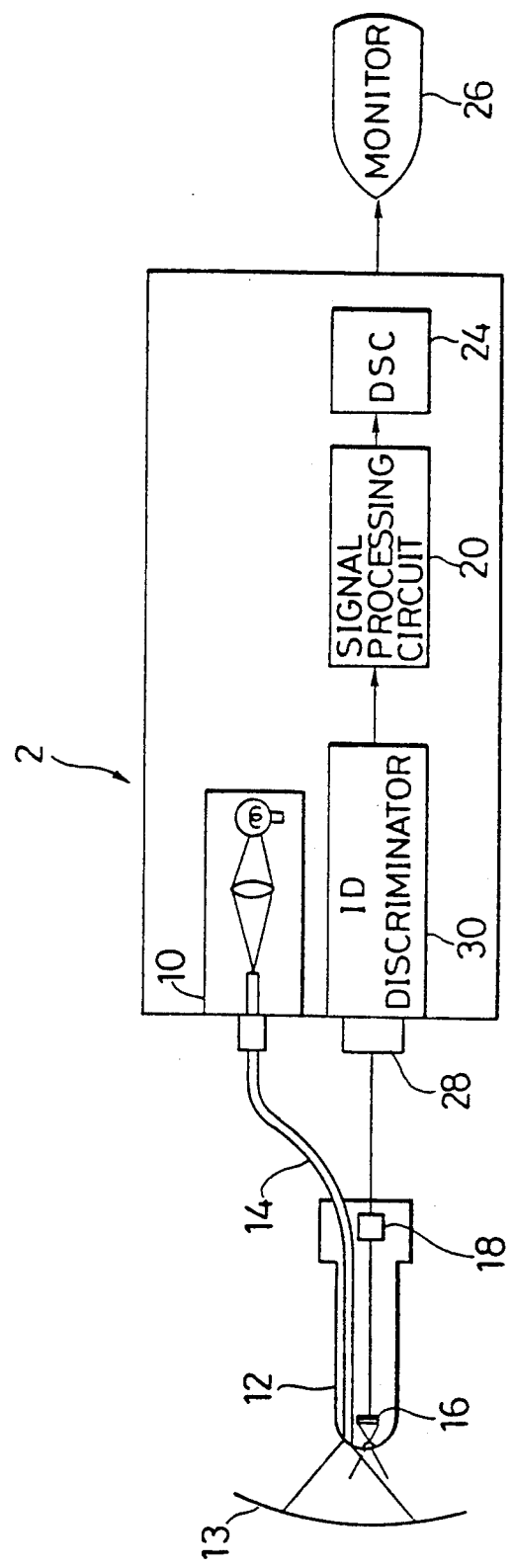
FIG. 1 is a general view schematically showing an endoscope system employing an articulated pipe according to an embodiment of the invention.

FIG. 1 shows an electronic endoscope system 2 employing an articulated pipe according to an embodiment of the invention. The electronic endoscope system 2 displays an image of a target area 13 in human body cavity on a monitor 26.

A light source 10 emits light, which is guided through a light guide 14 and emitted from an endoscope unit 12 to illuminate the target area 13 in a human body cavity.

A sensor 16 is attached to a head end of the endoscope unit 12. The sensor 16 may be a solid photographing element, such as a charge coupled device (CCD), for photographing the illuminated target area 13. The sensor 16 may also be supersonic receiver for receiving a supersonic signal from the target area 13. The supersonic signal is discharged from a supersonic oscillator 5.

The endoscope unit 12 includes a driving/receiving circuit 18, which controls the sensor 16. The sensor 16 converts photographed information into electric signals, which are transmitted through the driving/receiving circuit 18 to a signal processing unit 20.

The signal processing circuit 20 adjusts the optical characteristics of the photographed information according to the electric signals provided by the driving/receiving circuit 18. Output signals of the signal processing circuit 20 are received by a digital scan converter (DSC) 24. Output signals of the DSC 24 are received by the monitors 26, which displays a photographed image.

The endoscope unit 12 may be removably connected with a connector 28, and an ID discriminator 30 may discriminate and ID of the endoscope unit 12.

Figure 2:
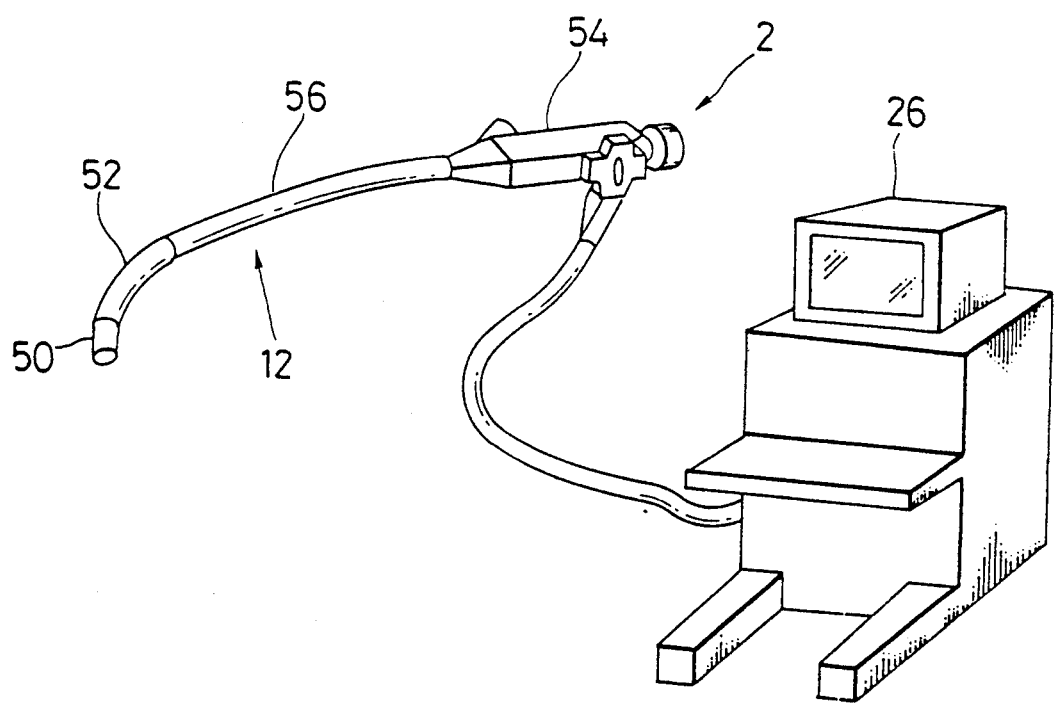
FIG. 2 is a perspective view showing the endoscope system.

As shown in FIG. 2, the endoscope 12 comprises a head end section 50 incorporating the CCD 16, an articulated pipe 52 that is vertically and horizontally bendable according to operator's manipulation, an operation section 54 manually operated by the operator, and an intermediate section 56 connecting the articulated pipe 52 with operation section 54 and accommodating cords such as the light guide 14. The head end 50 of the endoscope unit 12 is inserted into a body cavity and guided to a target area in the body cavity.

Figure 3:
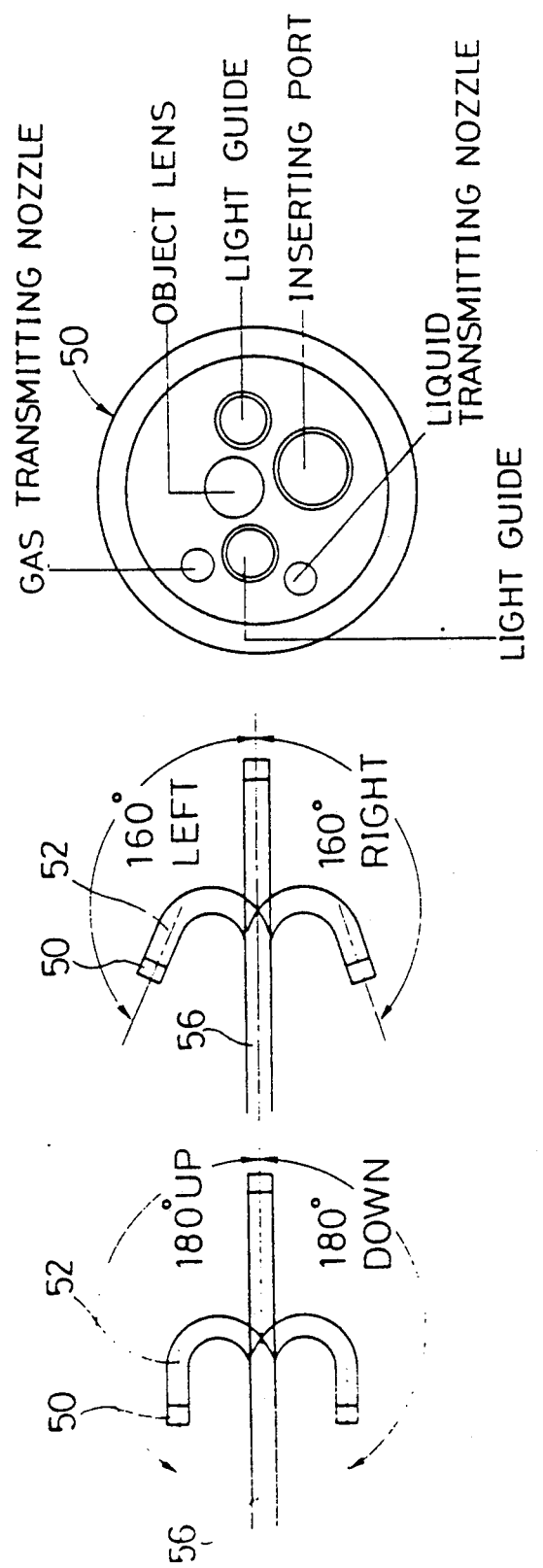
FIG. 3 is a view showing the bent states of the articulate pipe disposed at a head end of flexible tube of the endoscope system.

The maximum curvature of the articulated pipe 52 depend on the of target to be photographed and the of endoscope unit used. For example, for a large intestine endoscope, the articulated pipe 52 may be bent vertically for 180 degrees and horizontally for 160 degrees as shown in FIG. 3.

Figure 4:
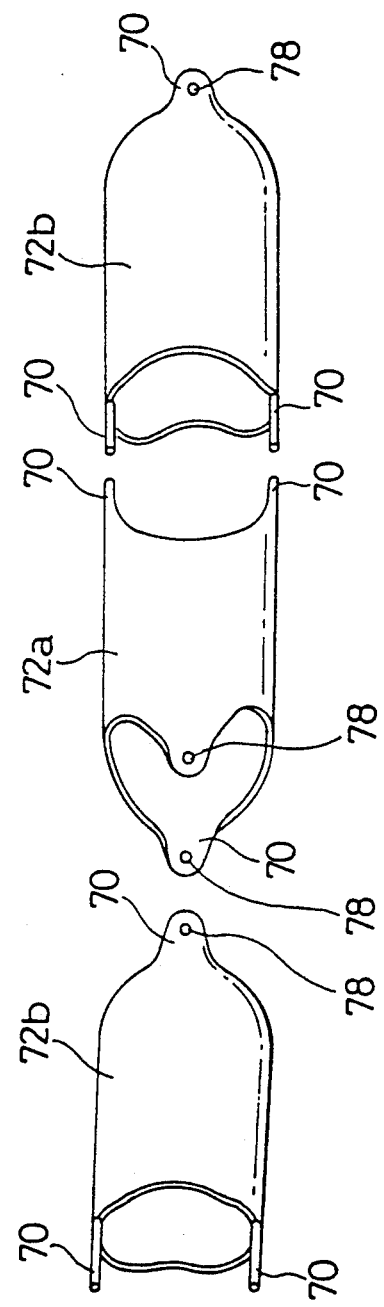
FIG. 4 is a perspective view showing articular chips according to an embodiment of the invention.

Such bending actions are achieved by the articulated pipe 52 composed of the articular chips 72a, 72b shown in FIG. 4. In is figure, articular chips 72a and 72b, each having joint portion 70, are joined one after another, so that the articulated pipe 52 may vertically and horizontally bend.

Figure 5:
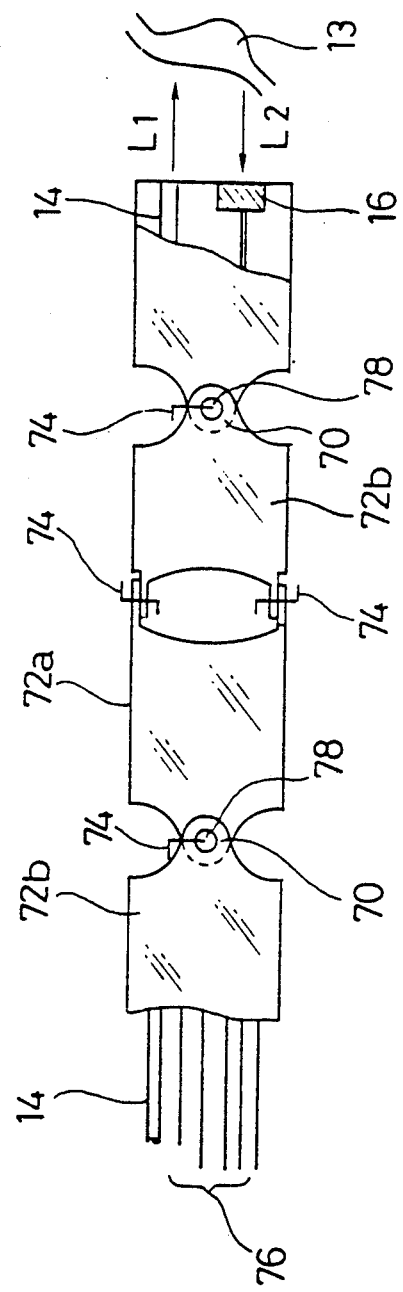
FIG. 5 is a general view showing the articulated pipe assembled from articulated chips.

FIG. 5 shows the articulated pipe 52 composed of the articular chip 72a and 72b accommodating the light guide 14, signal lines, control wires for controlling the curvature of the articulated pipe 52, etc. As shown in the figure, the articular chips 72a and 72b are joined in series with joint pins 74 to form the articulated pipe 52. The articular chips 72a and 72b are made of ceramics, while the joint pins 74 are made of shape-memory alloy.

FIG. 6 shows the articulated pipe 52 bent downward. In the figure, an upper control wire 76a is extended while a lower control wire 76b is tensed to bend the articulated pipe 52 downward. Similarly, the articulated pipe 52 may be bent upward, leftward, or rightward.

Each joint pin 74 joining articular chips 72a and 72b should allow the articular chips to smoothly move in rotation and keep a secure connection between the articular chips so that the joined articular chips are not easily separated from each other. In addition, the joint pin 74 should not damage the articular chips 72a and 72b when joining them together. To achieve these, the joint pins according to the present embodiment are made of shape-memory alloy.

The shape-memory alloy may be an Ni-Ti allow of 50:50 in atomic ratio, Ni-Al alloy, Cu-Al alloy, or Cu-Zn-Al alloy.

A shape memorized in each of the joint pins is selected in the way that the articular chips 72a and 72b should not easily disconnect once they are joined together by inserting the joint pins 74 into the joint holes of the articular chips. In addition, the memorized shape of the joint pins 74 should not interfere with other functions of the articulated pipe or the endoscope.

Figure 8A:
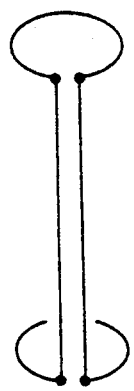
Figure 8B:
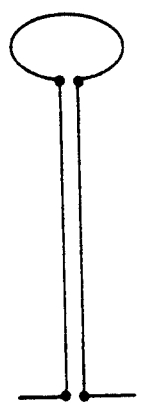
Figure 8C:
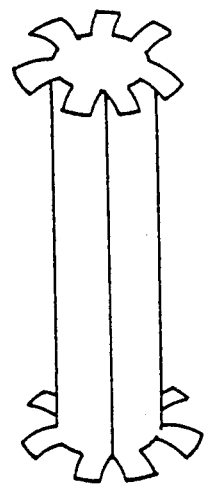

FIGS. 7(a) to 7(f) and 8(a) to 8(c) show shapes to be memorized in the joint pins according to the present embodiment. FIGS. 7(a), 7(b) and 7(f) show simple and convenient shapes. FIGS. 7(c), 7(d) and 7(e) show other preferable shapes. Shapes shown in FIGS. 8(a) and 8(b) are also acceptable. FIG. 8(c) shows an example of shapes that joint pins are made from a plate-like shape-memory alloy.

Figure 9A:
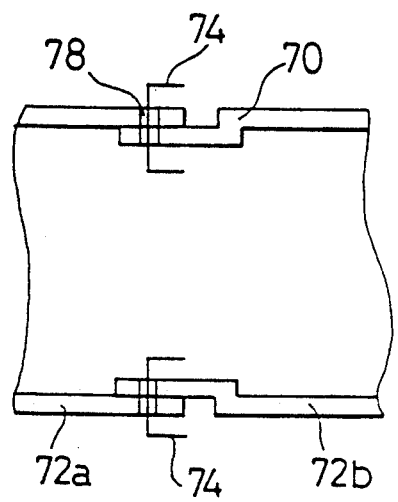
FIGS. 9(a) to 9(c) are views showing ways of joining the articular chips with the joint pins.
Figure 9B:
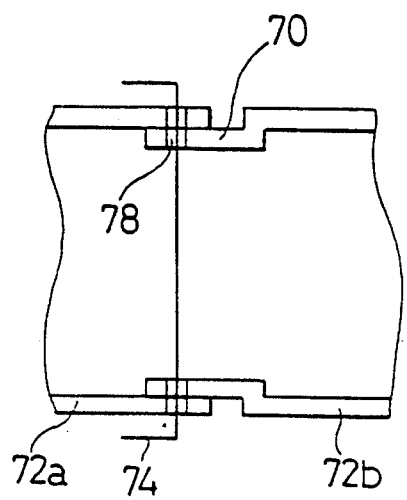
Figure 9C:
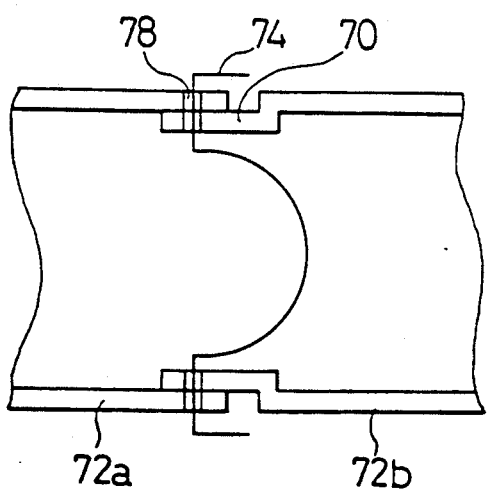

FIGS. 9(a) to 9(c) show how to join the articular chips with one another by means of the joint pins 74. In FIG. 9(a), a pair of the joint holes 78 of the articular chips 72a and 72b is joined together with the joint pin 74. In FIG. 9(b), vertically or horizontally aligned joint holes 78 of the articular chips 72a and 72b are joined together with the joint pin 74. In FIG. 9(c), the middle of the joint pin 74 is curved in order to easily pass the cords such as light guide 14 to be held inside the articular chips 72a and 72b.

The articulated pipe may serve such functions as a supersonic receiver or an endoscope. As a supersonic receiver, the articulated pipe receives a supersonic signal from a target area 13. The supersonic signal is discharged from a supersonic oscillator 15.

Figure 10:
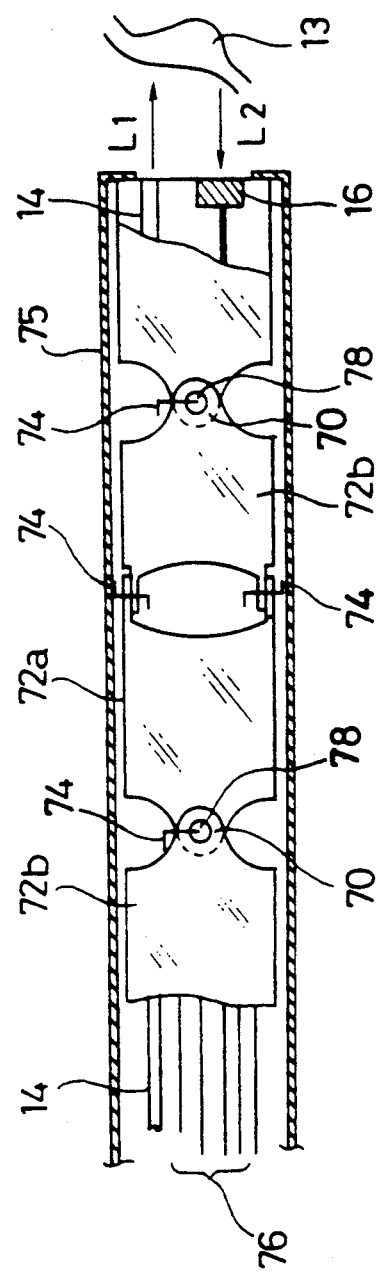
FIG. 10 shows an articulated pipe comprising a flexible tube 75 for covering the articular chips. In practical use, the pipe is covered with a flexible tube for insertion.
Figure 11:
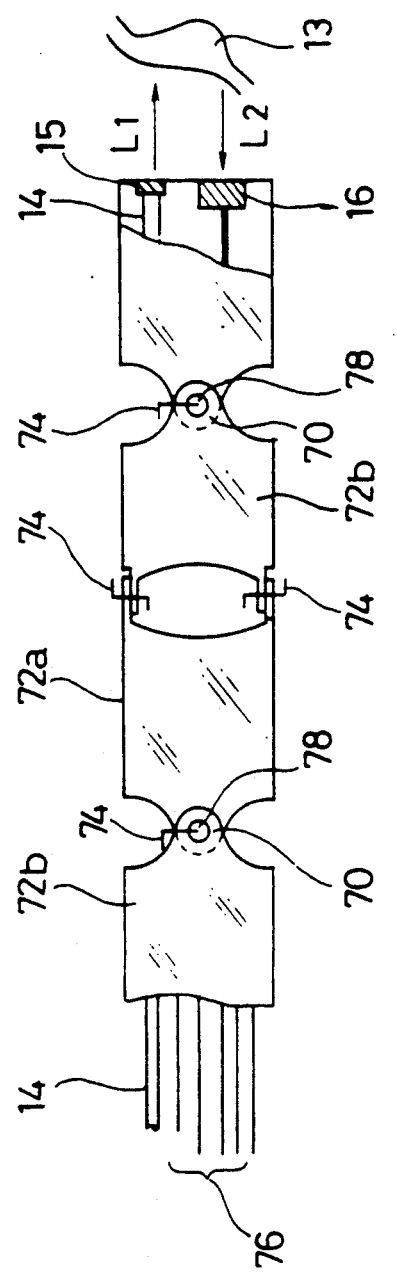
FIG. 11 shows an articulated pipe comprising a supersonic oscillator 15. The articulated pipe is used in this embodiment as a catheter. In such a case, supersonic oscillator 15 is positioned at the head end of the pipe, as shown in FIG. 11.

FIG. 10 shows an articulated pipe comprising a flexible tube 75 for covering the articular chips. In practical use, the pipe is usually covered with a flexible tube for insertion. FIG. 11 shows an articulated pipe comprising a supersonic oscillator 15. The articulated pipe may be used as a catheter. In such a use, it comprises a supersonic oscillator 15 at the head end of the pipe, as shown in FIG. 11.

A methods of joining the articular chips 72a and 72b with joint pin 74 will be explained.

The joint pin 74 are placed in a heating furnace according to a conventional technique, to memorize a predetermined shape in the joint pins 74 at a predetermined temperature. Thereafter, one end of each of the joint pin 74 having memorized the shape is straightened so that it may easily enter into the joint holes 78 the articular chips 72a and 72b.

Meanwhile, a core bar made of soft material such as styrene foam is inserted into the articular chips to temporarily fix the articular chips 72a and 72b. This helps easily inserting the joint pins 74 into the joint holes 78 of the articular chips.

After the joint pins 74 are inserted into the joint holes 78 of the articular chips temporarily fixed, they are placed in the heating furnace to restore the memorized shape of the straightened part of each of the joint pins 74. At this time, styrene foam shrinks due to heat and joint pins 74 gradually comes off from the styrene foam.

In this way, a number of the articular chips are joined with one another with the joint pins without applying dynamic shocks onto the articular chips.

Instead of temporarily fixing the articular chips with the styrene foam, the articular chips may be wrapped with a sheet of soft paper which is easily pierced by the straightened joint pins. After the joint pins are inserted and the memorized shape thereof is restored, the paper is burnt and removed.

The articular chips thus joined are not easily separated from one another even if the articulated pipe 52 is bent into any orientation. Excellent properties of the ceramics of the articular chips, therefore, are fully utilized in the endoscope.

The shape memorized in the joint pins 74 may be restored by using not only the heat furnace but also hot air, a soldering iron and such. The temperature of the heating process may be determined according to the components and the ratios of the components of the shape-memory alloy.

The joint pins may be made of not only the shape-memory alloy but also shape-memory resin.

In summary, according the present invention, ceramic articular chips are joined with one another without receiving shocks, no breakage occurs in the ceramic articular chips, and therefore, excellent properties of the ceramic of the articular chips are fully utilized. As seen in FIGS. 1, 2, and 10, the articulated pipe formed of ceramic articular chips joined to each other in series is covered with a flexible tube 75, as is needed for practical purposes.

Various modifications will become feasible for those skilled in the art after receiving the teaching of the present disclosure without departing from the scope thereof.

What is claimed is:

1. An articulated pipe having articular chips made of brittle material having joint portions, and joint pins for joining the joint portions of adjacent ones of the articular chips in series to form the articulated pipe which is flexible as a whole, the joint portions being oriented so that adjacent joint pins are orthogonal to one another for the articulated pipe bending in any direction, the joint pins being made of shape-memory material, an end of which is straight in an ambient temperature of easy insertion into a joint hole of the joint portion and an original bent form is restored at a high temperature for keeping the pins within the joint holder.

2. The articulated pipe according to claim 1, wherein the articular chips are made of a ceramic.

3. The articulated pipe according to claim 2, wherein each of the articular chips has a thin cylindrical shape whose size is sufficiently small to be inserted into and along a body cavity.

4. The articulated pipe according to claim 2, wherein each of joint pins is made of wire material memorizing a shape that prevents removal once fitted to the articular chips.

5. The articulated pipe according to claim 2, wherein each of the joint pins is made of a shape memory material that memorizes a shape that prevents removal of the pin from the associated joint portion once the material has returned to its original shape.

6. The articulated pipe according to claim 2, wherein the shape-memory material is shape-memory alloy.

7. The articulated pipe according to claim 2, wherein the shape-memory is shape-memory resin.

8. The articulated pipe according to claim 2, further including a flexible tube for covering the articular chips.

9. The articulated pipe according to claim 8, further including a photographing element at the head end of the articulated pipe, for use of said pipe as an endoscope.

10. The articulated pipe according to claim 8, further including a supersonic oscillator at the head end of the articulated pipe for use as a catheter.

11. The articulated pipe according to claim 8, wherein said articulated pipe carries a photographic element at its head, for use of the articulated pipe as an endoscope.

12. The articulated pipe according to claim 8, further including a supersonic oscillator at the head end thereof for use as a catheter.

* * * * *